(12) United States Patent
Deane et al.

(10) Patent No.: US 11,547,305 B2
(45) Date of Patent: Jan. 10, 2023

(54) METHOD AND SYSTEM FOR IMPROVED MOTION ROBUSTNESS DURING MEASUREMENT OF LOCALIZED ORAL INFLAMMATION

(71) Applicant: KONINKLIJKE PHILIPS N.V., Eindhoven (NL)

(72) Inventors: Steven Charles Deane, Cambridge (GB); Alan James Davie, Cambridge (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 314 days.

(21) Appl. No.: 16/768,947

(22) PCT Filed: Dec. 5, 2018

(86) PCT No.: PCT/EP2018/083567
§ 371 (c)(1),
(2) Date: Jun. 2, 2020

(87) PCT Pub. No.: WO2019/115303
PCT Pub. Date: Jun. 20, 2019

(65) Prior Publication Data
US 2021/0169339 A1 Jun. 10, 2021

Related U.S. Application Data

(60) Provisional application No. 62/597,623, filed on Dec. 12, 2017.

(51) Int. Cl.
*A61B 5/00* (2006.01)
*A61B 5/145* (2006.01)

(52) U.S. Cl.
CPC .......... *A61B 5/0088* (2013.01); *A61B 5/0075* (2013.01); *A61B 5/14542* (2013.01); *A61B 5/4552* (2013.01)

(58) Field of Classification Search
CPC . A61B 5/0088; A61B 5/0075; A61B 5/14542; A61B 5/455
See application file for complete search history.

(56) References Cited

U.S. PATENT DOCUMENTS

2010/0253773 A1   10/2010  Oota et al.
2010/0280392 A1*  11/2010  Liu ..................... A61B 5/0088
                                                600/475

(Continued)

FOREIGN PATENT DOCUMENTS

WO    2009036561 A1    3/2009
WO    2015069704 A1    5/2015

OTHER PUBLICATIONS

Zhang, Chunyang, et al. "Assessment of tissue oxygenation of periodontal inflammation in patients with coronary artery diseases using optical spectroscopy." BMC oral health 14.1 (2014): 1-8. (Year: 2014).*

(Continued)

*Primary Examiner* — Sean D Mattson

(57) ABSTRACT

A method for localizing gingival inflammation using an oral care device, comprising: emitting (520) light by one or more light emitters (42) of the oral care device; obtaining (530), at a first rate by one or more light detectors (40), reflectance measurements for a plurality of locations to generate first reflectance data; determining (540), by a controller (30) of the oral care device using the first reflectance data, whether the location comprises gingiva; obtaining (550), at a second rate by the one or more light detectors, reflectance measurements for each location determined to comprise gingiva to generate gingiva reflectance data, wherein the second rate is faster than the first rate; and determining (560), by the controller using the gingiva reflectance data, whether gingiva at that location is inflamed.

15 Claims, 6 Drawing Sheets

(56) References Cited

U.S. PATENT DOCUMENTS

| | | |
|---|---|---|
| 2013/0323673 A1 | 12/2013 | Hakomori et al. |
| 2013/0323674 A1 | 12/2013 | Hakomori et al. |
| 2015/0030989 A1 | 1/2015 | Soukos et al. |
| 2015/0305670 A1* | 10/2015 | Spruit .................... A61B 5/742 |
| | | 433/27 |
| 2016/0270716 A1* | 9/2016 | Guan ................... A61B 5/7264 |

OTHER PUBLICATIONS

International Application and Written Opinion, International Application No. PCT/EP2018/083567, dated Feb. 28, 2019.

* cited by examiner

METHOD AND SYSTEM FOR IMPROVED MOTION ROBUSTNESS DURING MEASUREMENT OF LOCALIZED ORAL INFLAMMATION

This application is the U.S. National Phase application under 35 U.S.C. § 371 of International Application No. PCT/EP2018/083567, filed on 5 Dec. 2018, which claims the benefit of U.S. Provisional Application No. 62/597,623, filed 12 Dec. 2017. These applications are hereby incorporated by reference herein.

FIELD OF THE INVENTION

The present disclosure is directed generally to methods and systems for improved detection of localized gingival inflammation using an oral care device.

BACKGROUND

Proper tooth brushing, including length and coverage of brushing, helps promote long-term dental health. Many dental problems are experienced by individuals who either do not regularly brush their teeth or who do so inadequately, especially in a particular area or region of the oral cavity. Among individuals who do brush regularly, improper brushing habits can result in poor coverage of brushing and thus surfaces that are not adequately cleaned during a cleaning session, even when a standard brushing regimen, such as brushing for two minutes twice daily, is followed.

Indeed, it is estimated that 50% of the adult population in the United States is affected by periodontal disease, with severity of disease ranging from gingivitis to periodontitis. However, consumers are often not able to detect early signs of periodontal disease. Accordingly, such diseases may only be detected during dental visits when the disease is already advanced and significantly harder to treat.

Inflammation of tissues within the mouth is one of the key signs of periodontal disease. Detecting inflammation would signal the existence of a disease state, and would alert the individual to the need for treatment to address the issue. For example, inflammation of the gums can be reversible with proper home care if it is detected, while bone loss from periodontitis will require professional treatment. However, existing methods and devices are unable to adequately identify or quantify inflammation of tissues, particularly localized inflammation. For example, handheld devices enable poor detection of gingival inflammation, as these devices either analyze large areas of the mouth resulting in a large signal-to-noise ratio that interferes with detection, or require so many measurements that they are not user friendly. Additionally, the motion of a user's hand can result in artifacts and poor readings by a handheld device. As a result, periodontal disease is often not detected.

Accordingly, there is a continued need in the art for oral care methods and devices that account for the motion of a user's hand during the detection of localized gingival inflammation.

SUMMARY OF THE INVENTION

The present disclosure is directed to inventive methods and systems for detecting tissue inflammation using an oral care device. Various embodiments and implementations herein are directed to an oral care device configured to obtain measurements of gingival tissue to identify localized gingival inflammation. The oral care device comprises a sensor with a configuration of one or more light emitters and one or more photodetectors or imagers to obtain information about gingival tissue at a plurality of sampled locations. The device obtains sensor data at a first rate to determine which of the sampled locations comprise gingiva, and then obtains sensor data at a second, faster rate for regions determined to comprise gingiva. The device uses this data to determine whether gingiva at that location is inflamed. According to an embodiment, the oral care device alerts the user in real-time or via a post-cleaning report to the existence of inflammation, and can optionally provide localization information to the user.

Generally in one aspect, a method for localizing gingival inflammation within a user's mouth using an oral care device is provided. The method includes: (i) emitting light by one or more light emitters of the oral care device; (ii) obtaining, at a first rate by one or more light detectors, a reflectance measurement for a plurality of locations within the user's mouth to generate first reflectance data for each of the plurality of locations; (iii) determining for each of the plurality of locations, by a controller of the oral care device using the first reflectance data, whether the location comprises gingiva; (iv) obtaining, at a second rate by the one or more light detectors, reflectance measurements for each location determined to comprise gingiva to generate gingiva reflectance data, wherein the second rate is faster than the first rate; and (v) determining, by the controller using the gingiva reflectance data, whether gingiva at that location is inflamed.

According to an embodiment, the method further includes the step of providing information regarding whether gingiva at a location comprises inflammation.

According to an embodiment, the method further includes the step of determining, from reflectance data generated at the first rate, whether the oral care device has moved. According to an embodiment, the step of determining whether the oral care device has moved comprising comparing reflectance data generated at the first rate to the first reflectance data for one or more of the plurality of locations.

According to an embodiment, a ratio of the first rate to the second rate is 1:3. According to an embodiment, a ratio of the first rate to the second rate is 1:10.

According to an embodiment, the step of determining whether gingiva at a location is inflamed comprises determining an approximate tissue oxygenation level of the gingiva at each of the remaining plurality of locations, wherein a low tissue oxygenation level indicates gingiva inflammation.

According to an embodiment, the one or more light emitters and the one or more light detectors are positioned such that the surface at each of the plurality of locations is not directly illuminated by the one or more light emitters.

According to an aspect, a device configured to localize gingival inflammation within a user's mouth is provided. The device comprises: (i) a light emitter configured to emit light; (ii) a light detector configured to obtain, at a first rate, reflectance measurements for a plurality of locations within the user's mouth to generate first reflectance data for each of the plurality of locations; and (iii) a controller configured to determine from the first reflectance data, for each of the plurality of locations, whether the location comprises gingiva; wherein the light detector is further configured to obtain, at a second rate, reflectance measurements for each location determined to comprise gingiva to generate gingiva reflectance data, wherein the second rate is faster than the first rate; and wherein the controller is further configured to determine from the gingiva reflectance data, whether gingiva at that location is inflamed.

According to an embodiment, the device further comprises a user interface configured to provide information regarding whether gingiva at a location comprises inflammation.

According to an embodiment, the controller is further configured to determine, from reflectance data generated at the first rate, whether the oral care device has moved. According to an embodiment, the controller is configured to determine whether the oral care device has moved by comparing reflectance data generated at the first rate to the first reflectance data for one or more of the plurality of locations.

As used herein for purposes of the present disclosure, the term "controller" is used generally to describe various apparatus relating to the operation of an oral care apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a method and device for detecting gingival inflammation using an oral care device. More generally, Applicant has recognized and appreciated that it would be beneficial to provide a system to detect localized tissue inflammation. Accordingly, the methods described or otherwise envisioned herein provide a device such as an oral care device configured to obtain measurements of gingival tissue. The oral care device comprises one or more of a variety of sensor arrays having at least one light emitter and at least one photodetector or imager to obtain information about gingival tissue at a plurality of sampled locations. The device obtains sensor data at a first rate to determine which of the sampled locations comprise gingiva, and then obtains sensor data at a second, faster rate for regions determined to comprise gingiva. The device uses this data to determine whether gingiva at that location is inflamed. The oral care device can then report that information to the user or a third party.

The embodiments and implementations disclosed or otherwise envisioned herein can be utilized with any oral device, including but not limited to a toothbrush, a flossing device, an oral irrigator, or any other oral device. For example, one application of the embodiments and implementations herein is to assess inflammation of gingival tissues using a specialized handheld oral inflammation detection device. Another application is to assess inflammation of gingival tissues using an oral care. However, the disclosure is not limited to a device such as described herein, and thus the disclosure and embodiments disclosed herein can encompass any oral device.

Figure 1:
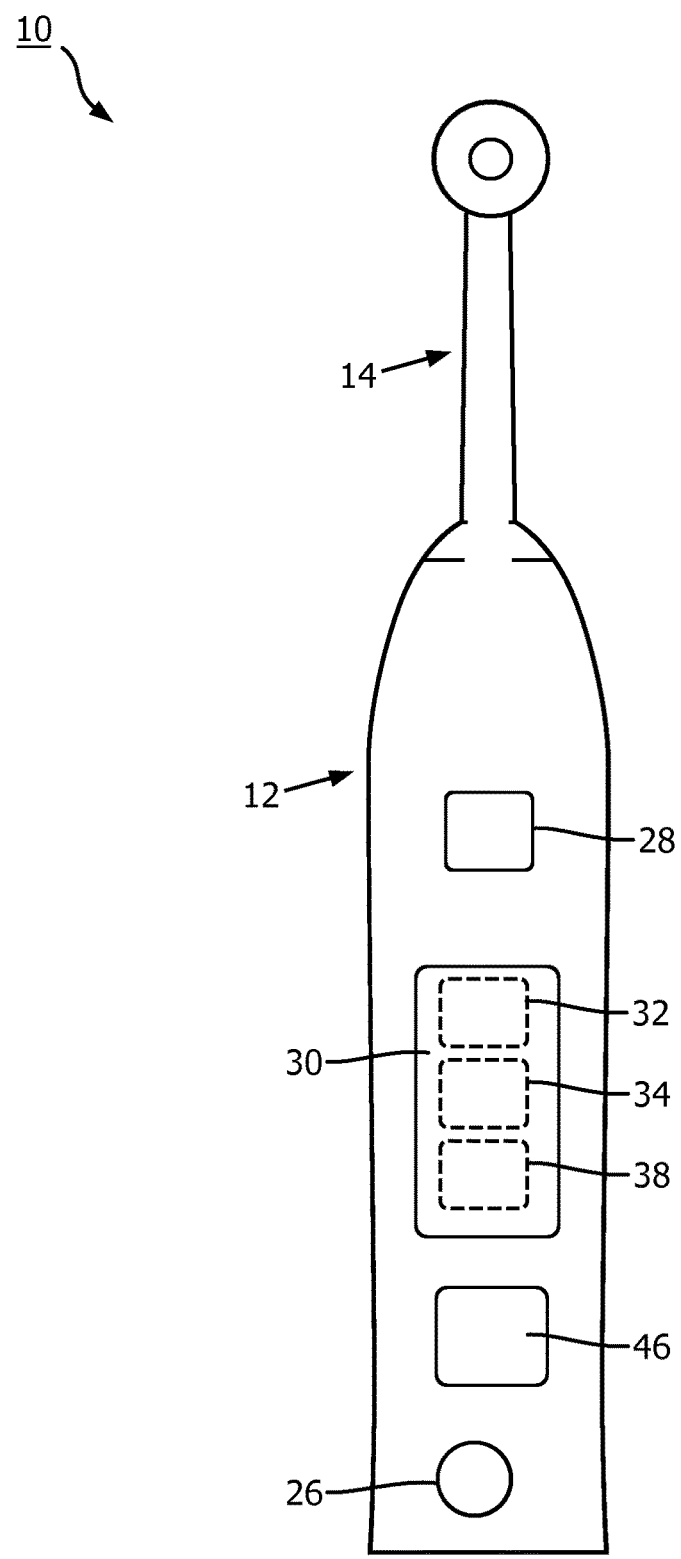
FIG. 1 is a schematic representation of an oral care device, in accordance with an embodiment.

Referring to FIG. 1, in one embodiment, is an oral care device 10 with a body portion 12 and a nozzle member 14 mounted on the body portion. According to an embodiment, nozzle member 14 may be configured to allow the passage of pressurized liquid and/or air from a reservoir in the body 12 (not shown) to the nozzle head where it is applied to the user's interdental regions. Nozzle member 14 can be detachably mounted onto body portion 12 such that the nozzle can periodically be replaced with a new one when a component of the device is worn out or otherwise requires replacement.

Body portion 12 is further provided with a user input 26. The user input 26 allows a user to operate the oral care device 10, for example to turn the oral care device on and off. The user input 26 may, for example, be a button, touch screen, or switch.

Oral care device 10 optionally includes one or more sensors 28. Sensor 28 is shown in FIG. 1 within body portion 12, but may be located anywhere within the device. Sensor 28 may be used to characterize the orientation and displacement of the device. According to an embodiment, these sensors provide information about the position of the device with respect to a user's body part, a fixed point, and/or one or more other positions. According to an embodiment, sensor 28 is disposed in a predefined position and orientation in the oral cleaning device 10, and the nozzle is in a fixed spatial relative arrangement to sensor 28. Therefore, the orientation and position of the nozzle can be easily determined based on the known orientation and position of the sensor 28.

The information generated by the first sensor 28 is provided to a controller 30. Controller 30 may be formed of one or multiple modules, and is configured to operate the oral cleaning device 10 in response to an input, such as input obtained via user input 26. According to an embodiment, the sensor 28 is integral to the controller 30. Controller 30 can comprise, for example, at least a processor 32, a memory 34, and a connectivity module 38. The processor 32 may take any suitable form, including but not limited to a microcontroller, multiple microcontrollers, circuitry, a single processor, or plural processors. The memory 34 can take any suitable form, including a non-volatile memory and/or RAM. The non-volatile memory may include read only memory (ROM), a hard disk drive (HDD), or a solid state drive (SSD). The memory can store, among other things, an operating system. The RAM is used by the processor for the temporary storage of data. According to an embodiment, an operating system may contain code which, when executed by controller 30, controls operation of the hardware components of oral cleaning device 10. According to an embodiment, connectivity module 38 transmits collected sensor data, and can be any module, device, or means capable of transmitting a wired or wireless signal, including but not limited to a Wi-Fi, Bluetooth, near field communication, and/or cellular module.

According to an embodiment, oral care device 10 includes a user interface 46 configured to provide information to a user before, during, and/or after a care session. The user interface 46 can take many different forms, but is configured to provide information to a user. For example, the information can be read, viewed, heard, felt, and/or otherwise interpreted concerning inflammation of one or more tissues within the mouth. According to an embodiment, the user interface 46 provides feedback to the user that includes information about where tissues are inflamed, and/or how much inflammation is present. Accordingly, the user interface may be a display that provides information to the user, a haptic mechanism that provides haptic feedback to the user, a speaker to provide sounds or words to the user, or any of a variety of other user interface mechanisms. For example, the system may provide feedback via a smartphone app, a website, or via any other interface configured to share information with the user.

Figure 2:
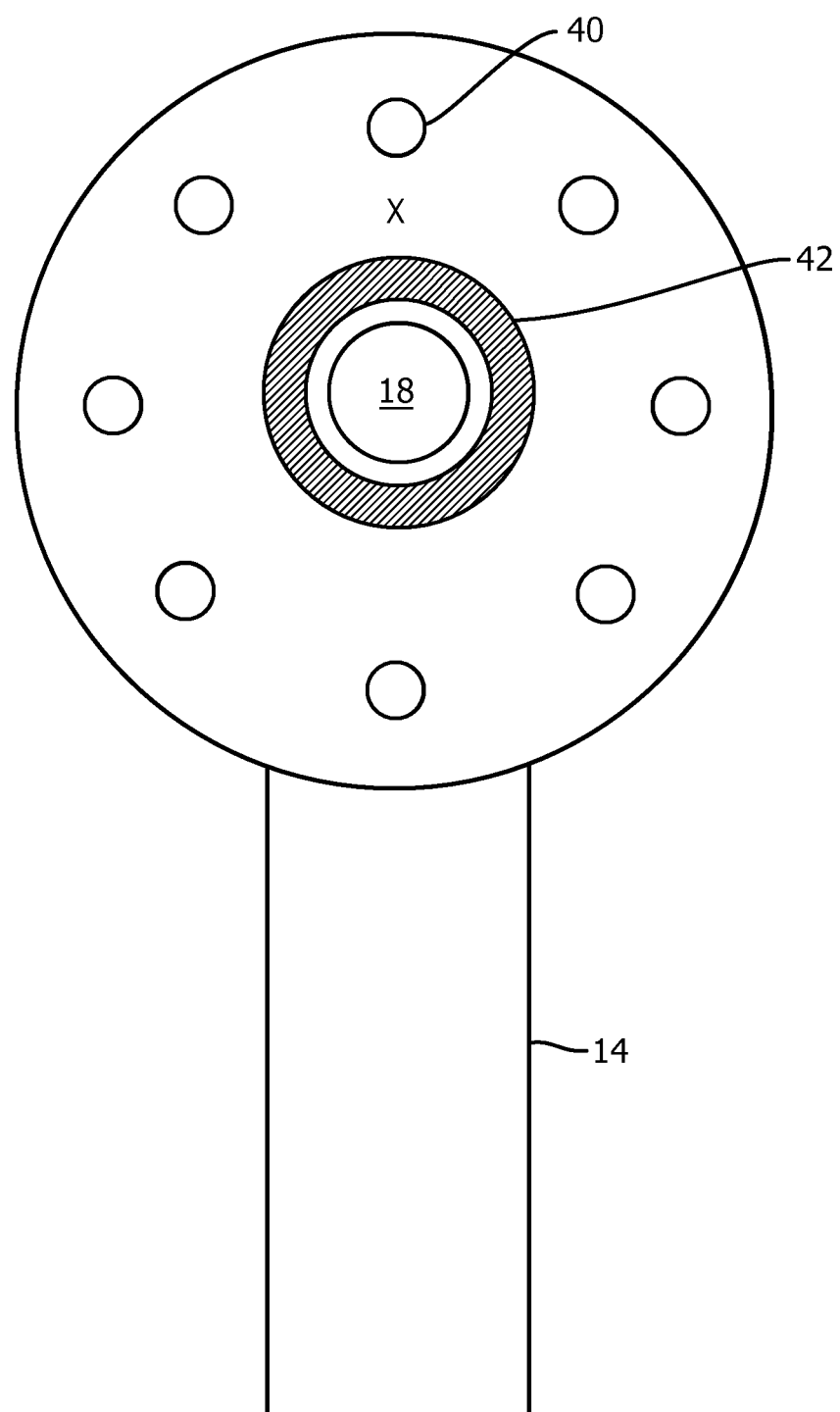
FIG. 2 is a schematic representation of a head of an oral care device, in accordance with an embodiment.

Referring to FIG. 2, in one embodiment, is a nozzle 14 of an oral care device. The nozzle includes a nozzle head portion, with a centrally-located guidance tip 18. According to one embodiment, the nozzle head comprises at least one light emitter 42 and at least one light receiver 40.

According to the embodiment depicted in FIG. 2, the light emitter 42 is a ring-shaped bundle of light-emitting fibers or a light-emitting light guide. The light emitter 42 is any light source, such as an LED light source, that emits light capable of facilitating the detection of gingival inflammation. According to an embodiment, the light emitters comprise combined light from a plurality of LEDs, and are connected by a light fiber or light guide from the LEDs to the light emitter on the surface of the oral care device. According to an embodiment the light source generates light in at least two wavelengths, such as 480 nm and 680 nm that allows for the characterization of oxygen saturation in human tissue, and hence the detection of localized inflammation. Generally, tissue exhibiting low tissue oxygenation indicates gingival inflammation.

Similarly, the one or more light receivers 40 are any light receivers capable of facilitating the detection of gingival inflammation. For example, according to an embodiment the light receivers are a photodetector or photodiode, or any other sensor capable of detecting light emitted by the light emitter 42. According to an embodiment, the light receivers are photodiodes connected to light fibers or light guides. Each light receiver may be configured to detect two or more wavelengths, or alternatively each light receiver may be configured to detect only a single wavelength. According to another embodiment, light receiver 40 is a pixel array configured to obtain one or more images of the tissue illuminated by the light emitted from the light emitter 42. The light receiver may comprise a plurality of detection fibers that are used simultaneously or may be time-multiplexed.

One advantage of the design of the oral care device in FIG. 2 is that the sensors are able to capture spatial information as well as gingival inflammation information. Since the information associated with each emitter-receiver couple comes from a unique tissue location, the localization of the inflammation is known.

In this embodiment, the guidance tip 18 provides a tactile feedback to the user, which facilitates proper interdental positioning near the gums. According to an embodiment, when properly positioned in the mouth, each light receiver 40 measures measures a different part of the tissue surface, which is approximately the location between the light emitter and the light receiver. For example, when placed on the junction between two teeth and the gingiva the light emitter will illuminate the whole area, and several light receivers 40 will be on the gingiva to detect inflammation, while others will be simultaneously placed on the teeth which can be easily distinguished from the measured spectral response.

According to an embodiment, many different configurations of light emitters 42 and light detectors 40 are possible. For example, one possible configuration is a ring of three to twelve light detectors around a single light emitter, with six to eight possibly being optimal depending on the size of the head of the oral care device. Alternatively, the device may comprise a ring of three to twelve light emitters around a single light detector. Many other configurations are possible.

The one or more light emitters 42 and light detectors 40 are positioned on device 10 such that the surfaces of the gingival tissue from which data is obtained are not directly illuminated by the light emitter. For example, referring to FIG. 2, the light emitter 42 emits light into the tissue in front of it, and light detector 40 obtains reflectance data from the tissue located at or very near the "X" shown on the device, although the light detector could also obtain reflectance data from the tissue located in front of it as well. According to an embodiment, therefore, the light emitters and the surfaces from which data is obtained are not overlapping. This is in contrast to a camera system in which imaged surfaces are directly illuminated. When a surface is directly illuminated, for example, detection or an image is dominated by near-surface scattering, which prevents the analysis of the gingival tissue as described herein.

Figure 3:
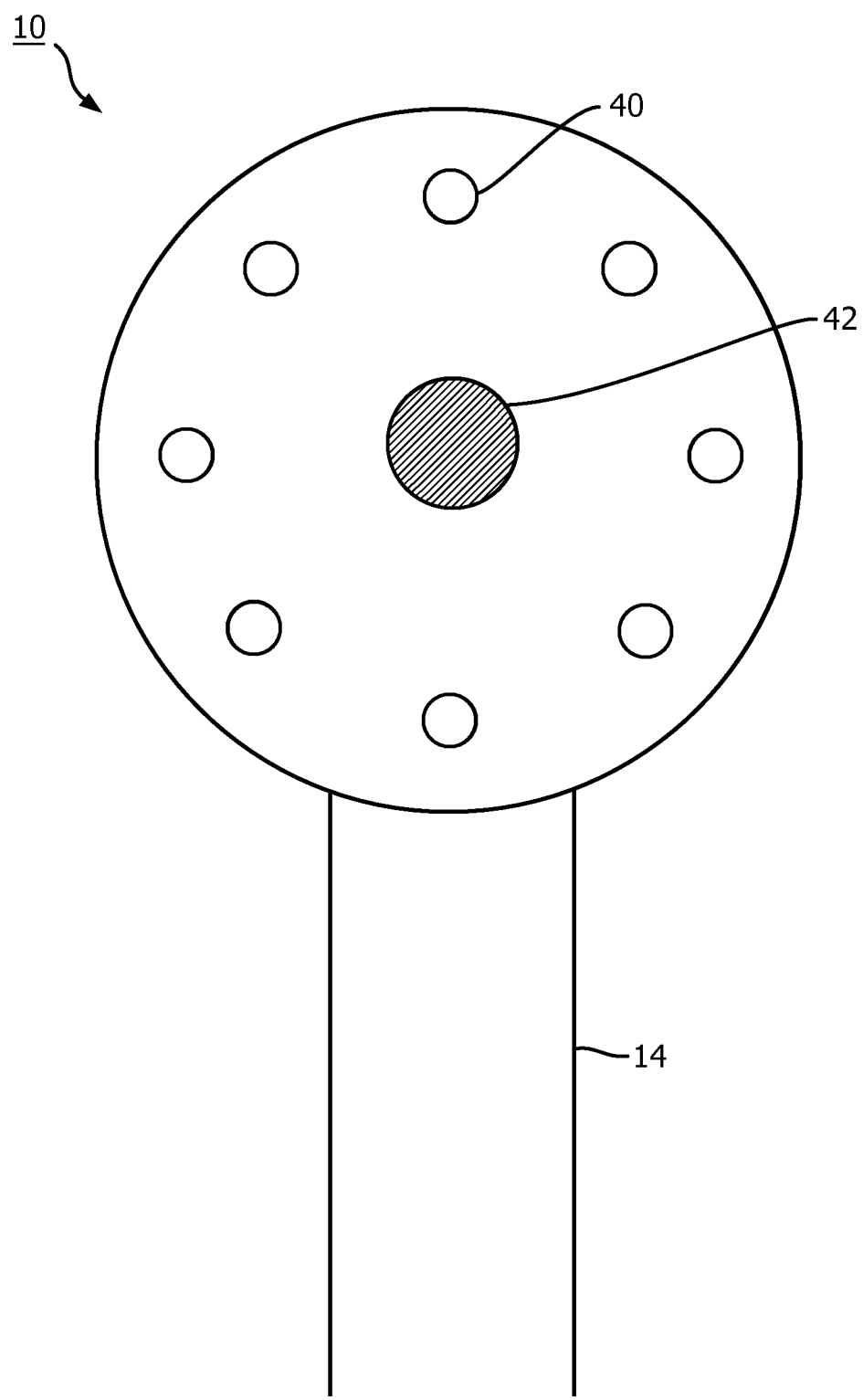
FIG. 3 is a schematic representation of a head of an oral care device, in accordance with an embodiment.

For example, referring to FIG. 3 is an embodiment of an oral care device 10 configured primarily to measure gingival inflammation. The oral care device comprises a head portion having a single centralized light emitter 42 and a plurality of light detectors 40. According to a similar embodiment, the device may comprise a single centralized light detector 40 and one or more light emitters 42.

Figure 4:
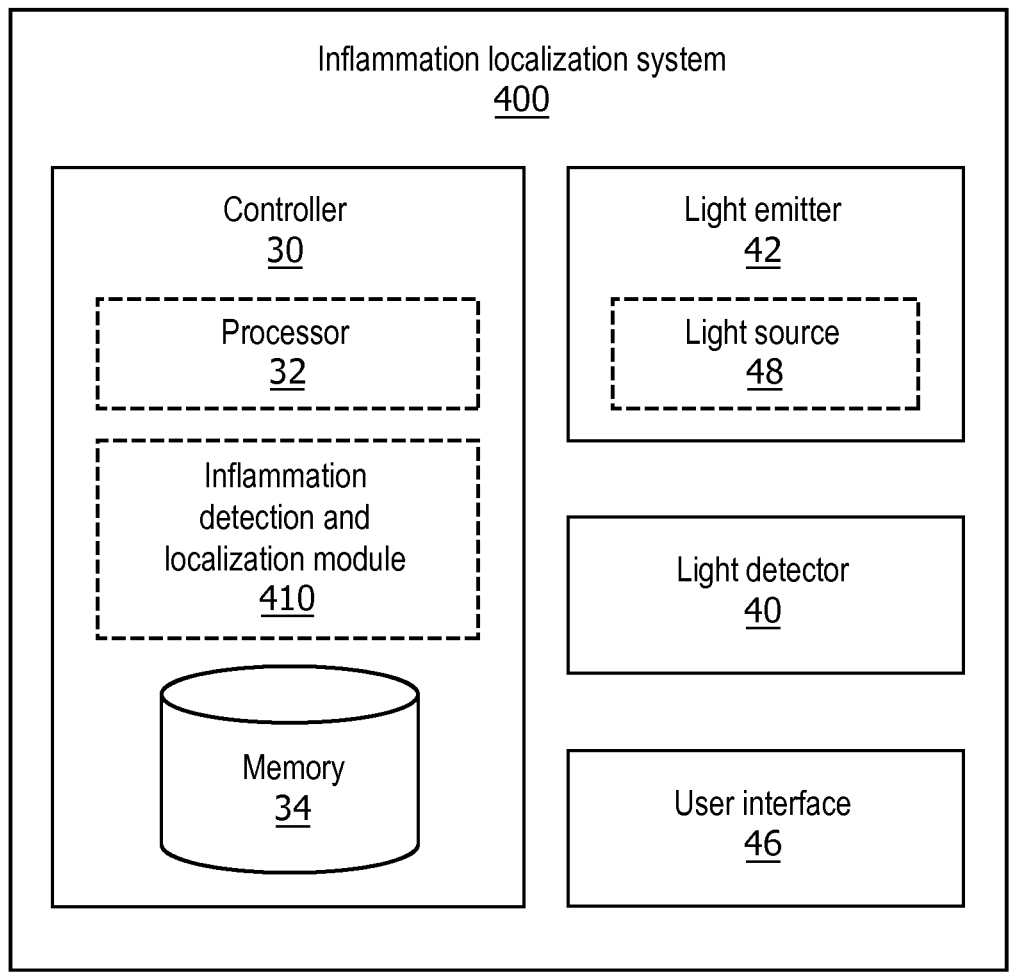
FIG. 4 is a schematic representation of an inflammation localization system, in accordance with an embodiment.

Referring to FIG. 4, in one embodiment, is an inflammation localization system 400. According to an embodiment, inflammation localization system 400 includes a controller 30 comprising a processor 32 and a memory 34. The inflammation localization system also comprises one or more light emitters 42 with one or more light sources 48. Inflammation localization system 400 includes one or more light detectors 40 which provide sensor data to the controller 30. Controller 30 of inflammation localization system 400 includes an inflammation detection and localization module 410. The inflammation detection and localization module analyzes sensor data from the one or more light detectors 40, and optionally device localization information from sensor 28, and determines whether the analyzed tissue is inflamed and where that tissue is located. The inflammation localization system also includes a user interface 46, which provides information to the user about the status and/or location of the tissue. User interface 46 can be or can comprise a feedback module that provides direct feedback to the user via a haptic signal, audio signal, visual signal, and/or any other type of signal.

According to an embodiment, inflammation localization system 400 can be implemented in any device configured to come into proximity with tissues that can be quantified. For example, inflammation localization system 400 can be implemented as another oral care device such as a toothbrush, an oral irrigator, a tongue cleaner, or any other oral care device.

Figure 5:
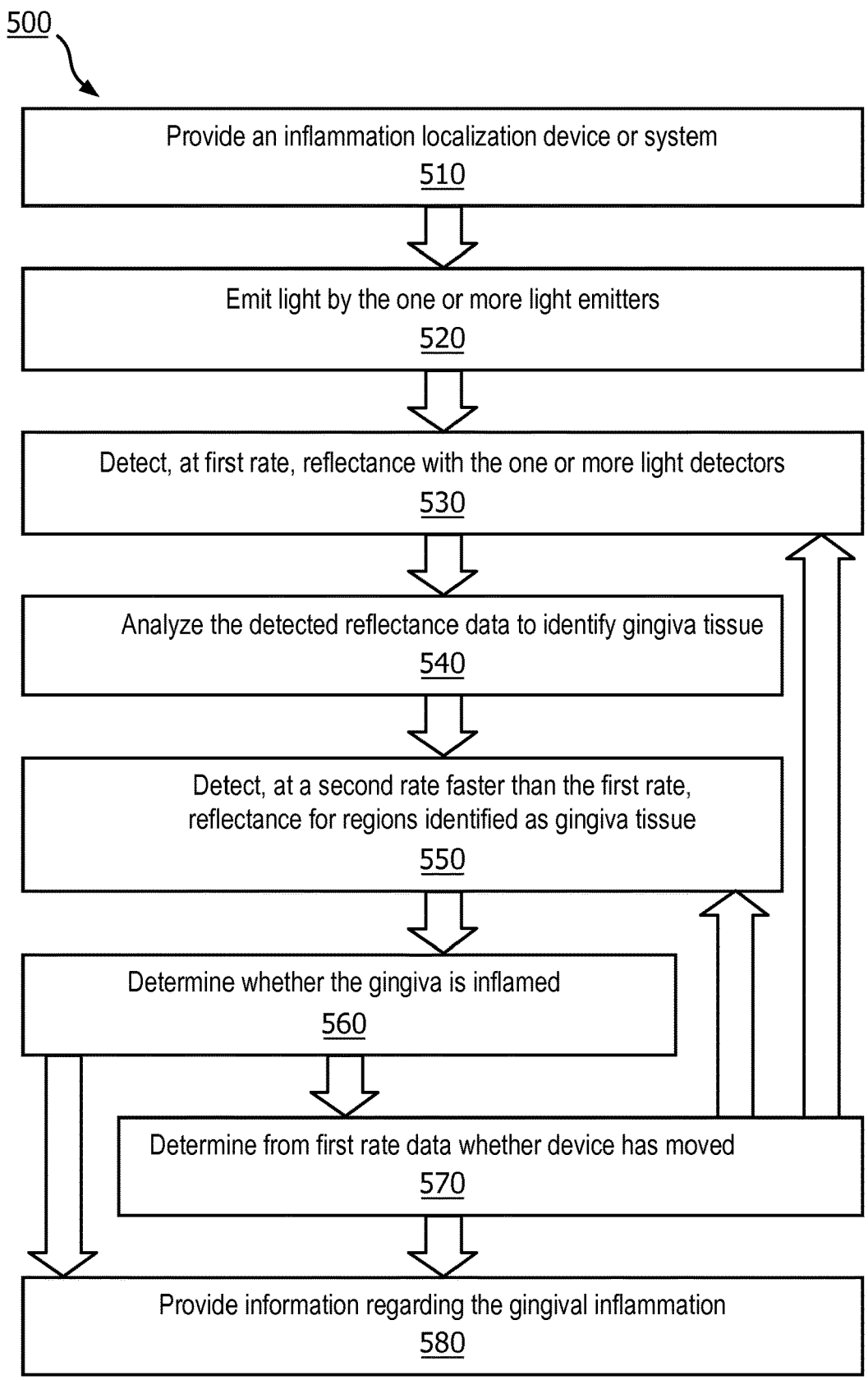
FIG. 5 is a flowchart of a method for localizing gingiva inflammation, in accordance with an embodiment.

Referring to FIG. 5, in one embodiment, is a flowchart of a method 500 for localizing inflammation of gingival tissue within a user's mouth. In step 510, an inflammation localization system is provided. The inflammation localization system may be any of the devices or systems described or otherwise envisioned herein. Generally, the inflammation localization system will comprise one or more light emitters 42, one or more light detectors 40, and an inflammation detection and localization module 410 configured to analyze the data from the one or more light detectors. Many other components and configurations are possible. Although method 500 is described within the framework of an oral care device 10, the method can be implemented using any other inflammation localization analysis system.

At step 520 of the method, one or more light emitters 42 emits light, a beam of each of which impacts the gingival tissue. According to an embodiment, the emitted light only indirectly impacts the gingival tissue that is analyzed by the light detector 40. The light emitted by the light emitter can be one or multiple wavelengths. Accordingly, a light emitter may comprise one or more light sources. The light emitter may emit light periodically or continuously, or may emit light only in response to a trigger.

At step 530 of the method, at least one light detector 40 obtains reflectance data, such as reflectance from the surfaces reflecting light emitted by the light emitters 42. The light detector may obtain a single data point or may obtain multiple data points over time. The light detector may obtain data continuously or may only obtain data in response to a trigger. For example, the light detector may be triggered to obtain sensor data in response to activation of a light emitter.

As discussed herein, the light detector 40 is positioned in a non-overlapping position relative to the light emitter 42 such that the detected tissue is only indirectly illuminated by the light from the light emitter. This configuration of the light detector(s) and the light emitter(s) results in a significant improvement in both the device and detection of inflammation. For example, the non-overlapping configuration described or otherwise envisioned herein maximizes the signal-to-noise ratio and enhances detection of localized gingival inflammation, among other benefits, by reducing near-surface scattering and other inhibitory factors.

According to an embodiment, light detector 40 obtains more than one color or spectral region for each location in order to provide a measured spectrum from which oxygen saturation can be calculated, which in turn indicates gum health (with higher oxygenation) or gingivitis (with lower oxygenation). The number of color channels may be as low as two, or could be a detailed spectrum comprising hundreds of channels. According to one embodiment, four to eight channels may be optimal. The color channels can be defined by narrow band light sources, such as LEDs, combined with wide band detectors such as photodiodes. Alternatively, the color channels can be defined by broad band light sources such as white LED combined with narrow band detectors such as photodiodes with narrow band filters, a color filter array, and other photodiodes configurations, among many other possible configurations of the system.

However, many microcontrollers typically have only one analog to digital converter, so in the case of broadband source and narrow band detection, sequential sampling may be needed to avoid increased component costs, additional space required for analog sample and hold circuits, and/or extra analog to digital converter channels.

Figure 6:
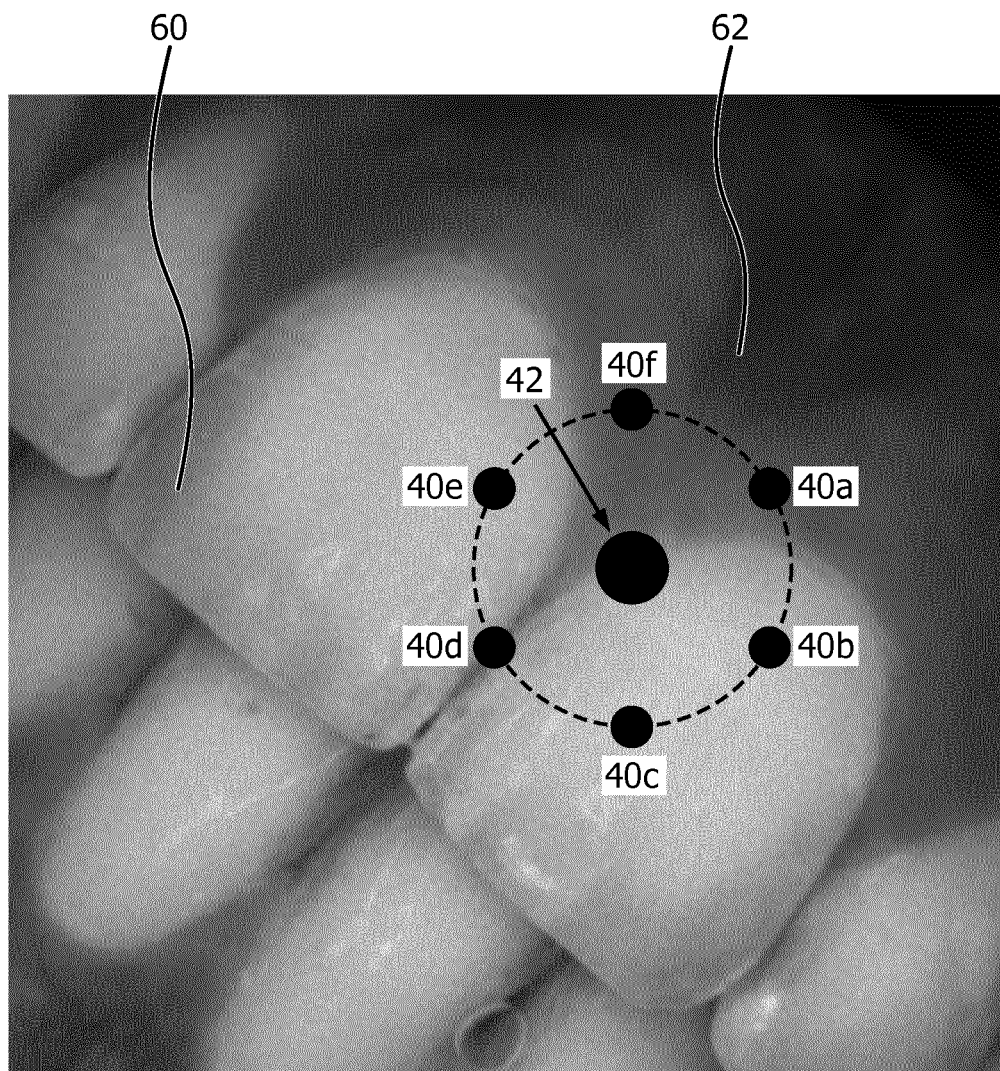
FIG. 6 is a schematic representation of portions of an oral care device positioned within a mouth, in accordance with an embodiment.

Accordingly, the at least one light detector 40 can be configured, programmed, or designed to obtain reflectance measurements at a first rate to identify whether a surface comprises gingiva. Referring to FIG. 6, for example, is a schematic representation of a user's teeth 60 and gingiva tissue 62. Aligned over the gingival and teeth tissues is an oral care device (not shown) with a plurality of light detectors 40*a*-*f* and a light emitter 42. FIG. 6 depicts an example of approximate locations where the light emitter will emit light into the tissue, and the light detectors will detect the emitted light. At step 530 of the method, each light detector 40*a*-*f* obtains reflectance measurements at a first rate for the location corresponding to that light detector. Referring to FIG. 6, for example, light detectors 40*a* and 40*f* are located over gingiva, while the remaining light detectors are located over teeth.

At step 540 of the method, controller 30 of oral care device 10 analyzes the obtained reflectance data to determine which of the plurality of analyzed locations are and/or are not gingiva. For example, the light detectors 40 provide the obtained reflectance data to controller 30 where it is analyzed by processor 32 and/or inflammation detection and localization module 410, and/or stored in memory 34 for future analysis.

According to one embodiment, the inflammation detection and localization module 410, which can be implemented as an algorithm, analyzes the obtained reflectance data in one or more steps. For example, as an initial step, the module rejects potential outliers in the data. Outliers may include spurious measurements, as well as reflectance data from objects that are likely not gingival tissues, such as food debris, teeth, and other objects. Since the absorption spectra of objects such as teeth and food debris vary considerably from the absorption spectra of gingival tissue, the two can be distinguished. According to an embodiment, outliers are detected at points with absorption spectra that do not correspond to gingival tissue, essentially not showing the sharp spectral characteristics of hemoglobin absorption.

According to an embodiment, inflammation detection and localization module 410 determines a reflectance ratio of two different wavelengths. Using sample data of spectra obtained at 550 nm and 660 nm, for example, a ratio of reflectance would provide values of 2.38 for gingival tissue and 1.21 for teeth. Similarly, a ratio of reflectance between a blue wavelength (400 nm to 480 nm) and a green wavelength (480 nm to 550 nm) would provide values of 5.96 for gingival tissue and 1.44 for teeth. Therefore, the inflammation detection and localization module 410 could be configured or programmed with predetermined thresholds to identify gingival tissue. According to an embodiment, the system compares the reflectance ratio to the predetermined threshold and characterizes the location as being gingiva or non-gingiva based on whether the determined reflectance ratio exceeds or does not exceed the predetermined threshold. As just one example, a threshold of 2 in both of the above examples would decipher between gingiva and non-gingiva; reflectance ratios above 2 are characterized as gingiva, and reflectance ratios below 2 are characterized as non-gingiva. The system would then discard data from non-gingiva and would only continue to analyze data obtained from gingiva.

According to another embodiment, at step 540 of the method the system analyzes the obtained reflectance data to determine which of the plurality of analyzed locations are and/or are not gingiva by weighting the reflectance data. For example, the system may apply a high weight to reflectance data indicative of gingiva, and/or may apply a low weight to reflectance data indicative of anything other than gingiva. A system configured to weight reflectance data may only apply a weight to reflectance data indicative of gingiva, may only apply a weight to reflectance data indicative of non-gingiva, or may apply weights to both conditions during an analysis. The weighting process may be a programmed or predetermined weighting process, or may be a machine-learned weighting process. Using a weighting process, the system may utilize the one or more weighting factors to focus on reflectance data indicative of gingiva for further analysis, including an analysis of possible inflammation.

In addition to removing non-gingiva reflectance data, and weighting gingiva and/or non-gingiva reflectance data, other methods of determining which of the plurality of analyzed locations are gingiva are possible.

At step 550 of the method, once the locations are identified as comprising gingiva or non-gingiva, the at least one light detector 40 of oral care device 10 obtains reflectance measurements at a second rate faster than the first rate. Reflectance measurements are obtained for these locations at a rate sufficient to determine gum health, such as by tissue oxygenation, even if there are any rapid movements of the probe compared to the gingiva, such as small tremors of the muscles in the hand positioning the probe.

Referring to FIG. 6, for example, light detectors 40a and 40f are located over gingiva and will be directed by the controller to obtain reflectance measurements at a second rate faster than the first rate. According to an embodiment, rather than obtaining reflectance measurements at equal rates for all regions, the measurements are divided into a slow scan cycle to determine areas of interest such as gingiva, and into a fast scan cycle for accurate measurements at a second, higher rate. The rate for the slow scan cycle need only be enough to determine whether the light detector is positioned over tooth or gingiva, such as while the user guides the device into position. The rate for the fast scan cycle needs to be fast enough to determine gum health as described or otherwise envisioned herein.

According to an embodiment, referring to FIG. 6 for example, a slow scan could use alternate time slots, such that it takes twelve time slots to measure the full circuit. The time slots between the slow measurements could be used for the fast scan cycle for the two locations (40a and 40f) identified from the slow measurement data as being gingiva. This would result in an increase of, in this example, 50% in the scan rate for the gingiva locations, for the same overall sampling rate. Of course, different numbers of spots can be used in the probe, and different ratios of the sampling rates between fast and slow groups. For example, if there are ten overall measurement spots, and two are selected for the fast group, then for low rates of slow measurement, the fast group may be measured up to five times (in general ratio of ('slow group'–'fast group')/'fast group') more rapidly than if measurements were equally distributed at the same total sampling rate. According to an embodiment, a ratio of slow to fast may be [slow rate]–[fast rate]/[fast rate].

Referring to TABLE 1, in one embodiment, is an example of sampling rates for an oral care device comprising eight light detectors 40. In this example, the slow rate obtains data in one out of every three time slots to detect gingiva and/or non-gingiva tissue. The fast rate obtains data in two out of every three time slots to determine whether the gingiva tissue is inflamed. As shown in TABLE 1, over the course of 25 time slots, reflectance measurements are obtained by light detectors a total of nine times (the first rate), while reflectance measurements are obtained by light detectors determined by the device to be located over gingiva a total of 16 times (the second rate), which is nearly three times the rate that the locations would be scanned at if all spots were sampled at the same rate. In other words, the scan repeats after the 16th measurement. If there was a uniform rate of sampling each of the eight sites would be sampled twice. However, according to an embodiment such as the one set forth in TABLE 1, the sites determined to be gingiva and sampled at the fast rate (i.e., sites 2 and 3) are sampled five times in the first 16 measurements, which is a 2.5 times increase in sampling.

TABLE 1

| Example of Sampling Rates for an Oral Care Device. | | | | | | | | | | | | | | | | | | | | | | | | | |
|---|---|---|---|---|---|---|---|---|---|---|---|---|---|---|---|---|---|---|---|---|---|---|---|---|---|
| Time slot | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
| Slow Rate | 1 | | | 4 | | 5 | | | 6 | | | 7 | | | 8 | | | 1 | | | | 4 | | | 5 |
| Fast Rate | | 2 | 3 | | 2 | 3 | | 2 | 3 | | 2 | 3 | | 2 | 3 | | 2 | 3 | | 2 | 3 | | 2 | 3 | |

In this example the locations identified to be located over gingiva were not included in the first rate sampling, and were only used for sampling at the second rate in the second rate time slots, in order to improve performance of the device. However, according to an embodiment, other configurations are possible. For example, the locations identified to be located over gingiva can also be included in sampling at the first, slower rate.

A time slot can be any period of time, and the ratio shown in TABLE 1 can be any ratio determined to maximize performance without a significant loss in measurement and reliability. For example, according to one embodiment, the slow rate is approximately 1 to 5 Hz, while the fast rate may be approximately 10 to 100 or 50 to 100 Hz, although many other rates are possible. As another example, according to one embodiment, the ratio of the slow rate to the fast rate may be 1:2, 1:3, or 1:10, although many other ratios are possible.

At step 560 of the method, the oral care device determines from the obtained reflectance measurements for each of the locations determined to comprise gingiva, whether gingiva at that location is inflamed. For example, the inflammation detection and localization module 410 analyzes the fast rate reflectance data from light detectors 40 at locations determined to comprise gingiva. This analysis can be done while the device is obtaining data, or may be completed after the oral care device has finished with a session, or it may be performed on demand from the user.

According to an embodiment, the inflammation detection and localization module 410 determines or characterizes an approximate tissue oxygenation level of the gingival tissue using the reflectance data. Since tissue oxygen saturation is significantly decreased in gingivitis and periodontitis locations compared to healthy locations, the module may select a signal exhibiting the lowest tissue oxygenation, which identifies the highest level of gingival inflammation. This may be performed, for example, by selecting the maximum value from a given set of data, or by taking the average of the X-top percentile from a given set of data, among other methods. The module may obtain this information, for example, at each locale for which data was obtained. The inflammation detection and localization module 410 will thus generate information about locations within the mouth where there is likely to be gingival inflammation.

At step 570 of the method, which may be performed at any point through the method, the oral care device analyzes data from the first rate scans to determine whether the device has moved. For example, the light detectors 40 may provide the obtained reflectance data to controller 30 where it is analyzed by processor 32 and/or inflammation detection and localization module 410. For example, the device may analyze reflectance measurements obtained at the first rate to determine which locations do and/or do not comprise gingiva, and may compare that to a previous measurement or determination to determine that the device has moved. This may comprise, for example, a determination that one or more light detectors are located over a different type of tissue. A light detector formerly located over gingiva may now be located over teeth, and a light detector formerly located over teeth may now be located over gingiva. This may be due to subtle movements of the user's hand, or due to the user intentionally moving the device to a new region or portion of the mouth.

Once there is a determination that the device has moved, the method can return to step 550 or any other step of the method, and may obtain reflectance measurements at the second rate for the locations now determined to be located over gingiva. This process may be continuously or periodically performed to ensure accurate and up-to-date reflectance measurements.

At step 580 of the method, the system or device optionally provides feedback to the user and/or a third-party regarding the inflammation localization information. The user interface 46 of the oral care device 10, for example, can provide direct and/or indirect feedback to the user while the oral care device is being used, or after a cleaning or scanning session. As an example, the device can provide direct feedback to the user after each measurement using audio, visual, haptic, and/or digital feedback whenever inflammation is detected.

According to another embodiment, the system or device may provide feedback to the user after a scanning session is complete. As an example, the system or device may provide feedback once a scanning session is complete by means of visual representation where the inflammation levels are displayed. The feedback may include, for example, a mouth map—using location sensing technology during measurement—either in their absolute form to show the inflammation levels or in relative forms to highlight one or more specific sites. According to an embodiment, the device can scale or otherwise rank inflammation levels using a variety of colors or other physical representations. For example, the user may only focus on areas of significant inflammation, or inflammation above a certain level.

According to an embodiment, the inflammation data is stored and/or communicated with a third party, either locally or remotely. For example, according to an embodiment, a patient may be instructed to use the oral care device during an appointment with a dental care professional, to assess inflammation. The inflammation information will then be communicated to the dental care professional, using a report or other mechanism. As another example, a user may collect inflammation data that is automatically or periodically transmitted to a remote healthcare professional or other intended or authorized entity where it can be analyzed continuously or during an appointment with the user.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for localizing gingival inflammation within a user's mouth using an oral care device, the method comprising:
    emitting light by one or more light emitters of the oral care device;
    obtaining, at a first rate by one or more light detectors, a reflectance measurement for each of a plurality of locations within the user's mouth to generate first reflectance data for each of the plurality of locations;
    determining for each of the plurality of locations, by a controller of the oral care device using the first reflectance data, whether the location comprises gingiva;
    obtaining, at a second rate by the one or more light detectors, a reflectance measurement for each location determined to comprise gingiva to generate gingiva reflectance data, wherein the second rate is faster than the first rate; and
    determining, by the controller using the gingiva reflectance data, whether gingiva at each location determined to comprise gingiva is inflamed.

2. The method of claim 1, further comprising the step of providing information regarding whether gingiva at a location comprises inflammation.

3. The method of claim 1, further comprising the step of determining, from a second reflectance data generated at the first rate, whether the oral care device has moved.

4. The method of claim 3, wherein the step of determining whether the oral care device has moved comprises comparing the second reflectance data generated at the first rate to the first reflectance data for one or more of the plurality of locations.

5. The method of claim 1, wherein a ratio of the first rate to the second rate is 1:3.

6. The method of claim 1, wherein a ratio of the first rate to the second rate is 1:10.

7. The method of claim 1, wherein the step of determining whether gingiva at one of the plurality of locations determined to comprise gingiva is inflamed comprises determining an approximate tissue oxygenation level of the gingiva at each of the other ones of the plurality of locations determined to comprise gingiva, wherein a low tissue oxygenation level indicates gingiva inflammation.

8. The method of claim 1, wherein the one or more light emitters and the one or more light detectors are positioned such that a surface at each of the plurality of locations is not directly illuminated by the one or more light emitters.

9. A device configured to localize gingival inflammation within a user's mouth, comprising:
    a light emitter configured to emit light;
    a light detector configured to obtain, at a first rate, reflectance measurements for a plurality of locations within the user's mouth to generate first reflectance data for each of the plurality of locations; and
    a controller configured to determine from the first reflectance data, for each of the plurality of locations, whether the location comprises gingiva;
    wherein the light detector is further configured to obtain, at a second rate, reflectance measurements for each location determined to comprise gingiva to generate gingiva reflectance data, wherein the second rate is faster than the first rate;
    wherein the controller is further configured to determine from the gingiva reflectance data, whether gingiva at each of the plurality of locations that is determined to comprise gingiva is inflamed.

10. The device of claim 9, further comprising a user interface configured to provide information regarding whether gingiva at one of the plurality of locations determined to comprise gingiva comprises inflammation.

11. The device of claim 9, wherein the controller is further configured to determine, from a second reflectance data generated at the first rate, whether the oral care device has moved.

12. The device of claim 11, wherein the controller is configured to determine whether the oral care device has moved by comparing the second reflectance data generated at the first rate to the first reflectance data for one or more of the plurality of locations.

13. The device of claim 9, wherein a ratio of the first rate to the second rate is 1:3.

14. The device of claim 9, wherein a ratio of the first rate to the second rate is 1:10.

15. The device of claim 9, wherein determining whether gingiva at one of the plurality of locations determined to comprise gingiva is inflamed comprises determining an approximate tissue oxygenation level of the gingiva at other ones of the plurality of locations determined to comprise gingiva, wherein a low tissue oxygenation level indicates gingiva inflammation.

* * * * *